United States Patent [19]

Sawada et al.

[11] Patent Number: 4,579,819

[45] Date of Patent: Apr. 1, 1986

[54] METHOD FOR PRODUCTION OF URSODEOXYCHOLIC ACID BY MEANS OF MICROBIAL TRANSFORMATION

[75] Inventors: Haruji Sawada, Osaka; Hisaharu Taguchi, Toyonaka, both of Japan

[73] Assignee: Kabushiki Kaisha Yakult Honsha, Higashishinbashi, Japan

[21] Appl. No.: 471,460

[22] Filed: Mar. 2, 1983

[30] Foreign Application Priority Data

Mar. 9, 1982 [JP] Japan ................................... 57-37116

[51] Int. Cl.4 .......................... C12P 33/06; C12R 1/77
[52] U.S. Cl. ...................................... 435/58; 435/929
[58] Field of Search ........................................... 435/58

[56] References Cited

U.S. PATENT DOCUMENTS 3,429,778  2/1969  Pan et al. ............................... 435/58
4,303,754  12/1981  MacDonald ........................... 435/58

OTHER PUBLICATIONS

Sawada et al., Applied and Environmental Microbiology, pp. 1249–1252, Dec. 1982.

Primary Examiner—Alvin E. Tanenholtz
Attorney, Agent, or Firm—Wenderoth, Lind & Ponack

[57] ABSTRACT

A one-step method of producing ursodeoxycholic acid by means of microbial transformation which comprises subjecting lithocholic acid to the action of a ursodeoxycholic acid producing microorganism.

5 Claims, 1 Drawing Figure

METHOD FOR PRODUCTION OF URSODEOXYCHOLIC ACID BY MEANS OF MICROBIAL TRANSFORMATION

FIELD OF THE INVENTION

The present invention relates to a method for production of ursodeoxycholic acid, and more specifically to a method for production of ursodeoxycholic acid, the final product, which comprises subjecting lithocholic acid, the starting material, to the action of one or more specific ursodeoxycholic acid producing microorganisms.

BACKGROUND OF THE INVENTION

Ursodeoxycholic acid is a bile acid wherein hydroxyl groups are located at the 3α and 7β positions of the steroid molecule and has the structural formula (I) shown below.

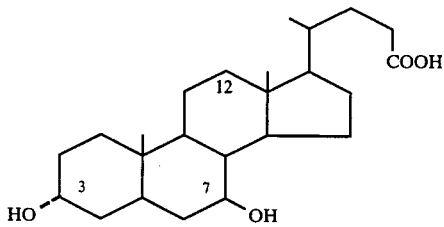

Ursodeoxycholic acid
(I)

Ursodeoxycholic acid is known as one of the traditional cholagogues. Since it was discovered that this material is effective to solubilize cholesterol gallstones, plenty of clinical data have been reported to show that the material is effective for therapy of cholesterol gallstone per os administration.

Since ursodeoxycholic acid is available in the bile of a bear, it is possible to extract it therefrom. It is unrealistic, however, to assume that the supply is sufficient to meet the entire medical demands particularly from the quantitative viewpoint. Accordingly, chemical synthesis processes have been employed for production of ursodeoxycholic acid.

One exemplary process for synthesis of ursodeoxycholic acid will be described below.

The first step is to methylate the carboxyl group of cholic acid (II), the starting material, the converting cholic acid (II) to methyl cholate (III), as shown below.

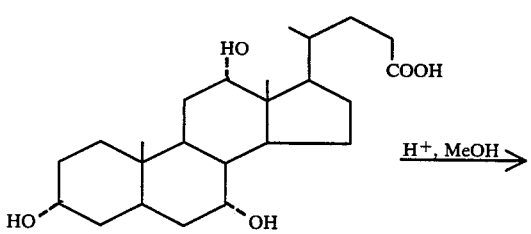

Cholic acid
(II)

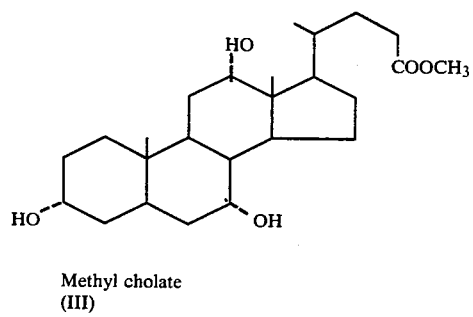

Methyl cholate
(III)

The second step is to acetylate the hydroxyl groups located at the 3α and 7α positions of methyl cholate (III) by adding acetic anhydride to the same to obtain 3α,7α-diacetoxy-12α-hydroxy-5β-methyl cholanate (IV), as shown below.

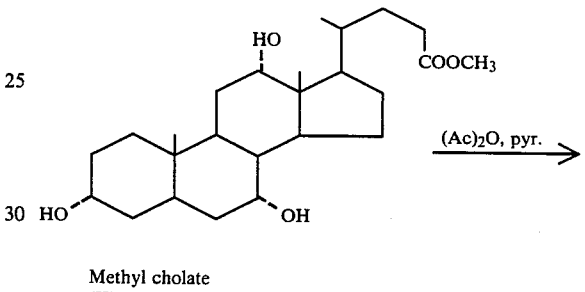

Methyl cholate
(III)

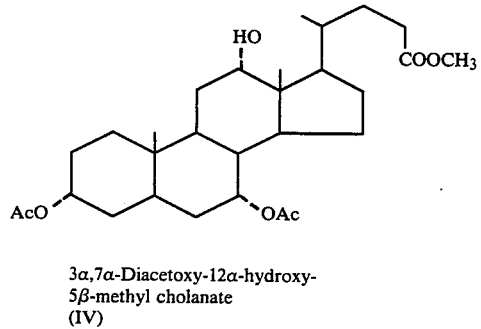

3α,7α-Diacetoxy-12α-hydroxy-
5β-methyl cholanate
(IV)

The third step is to oxidize the hydroxyl group located at the 12 position of 3α,7α-diacetoxy-12α-hydroxy-5β-methyl cholanate (IV) by adding chromic acid to the same to obtain 3α,7α-diacetoxy-12-keto-5β-methyl cholanate (V), as shown below.

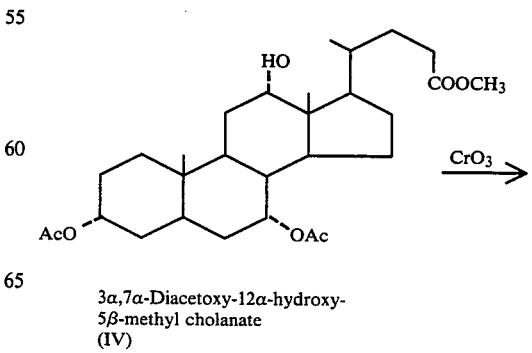

3α,7α-Diacetoxy-12α-hydroxy-
5β-methyl cholanate
(IV)

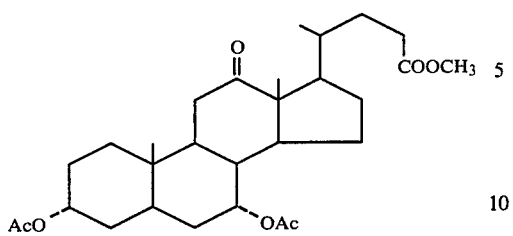

3α,7α-Diacetoxy-12-keto-
5β-methyl cholanate
(V)

The fourth step is to saponify 3α,7α-diacetoxy-12-keto-5β-methyl cholanate (V) to obtain 12-ketochenodeoxycholic acid (VI), as shown below.

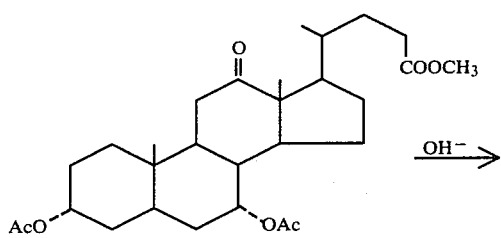

3α,7α-Diacetoxy-12-keto-
5β-methyl cholanate
(V)

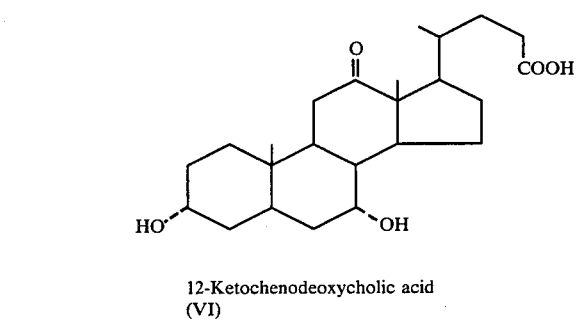

12-Ketochenodeoxycholic acid
(VI)

The fifth step is to reduce the carbonyl group located at the 12 position of 12-ketochenodeoxycholic acid (VI) by employing the Huang-Minlon modification to obtain chenodeoxycholic acid (VII), as shown below.

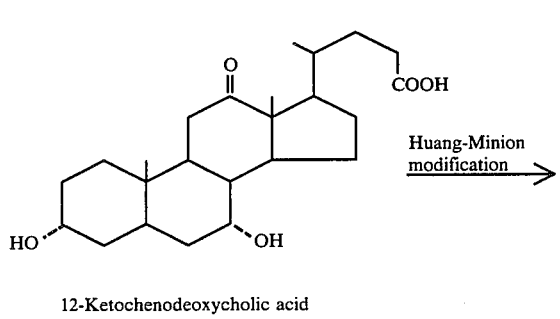

12-Ketochenodeoxycholic acid
(VI)

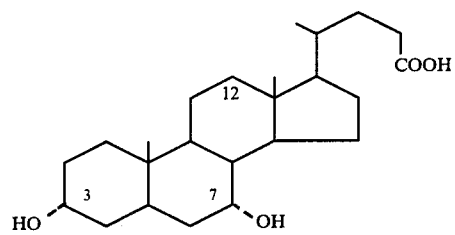

Chenodeoxycholic acid
(VII)

The sixth step is to oxidize the hydroxyl group located at the 7α position of chenodeoxycholic acid (VII) by adding N-bromosuccinimide to the same, thus obtaining 7-ketolithocholic acid (VIII), as shown below.

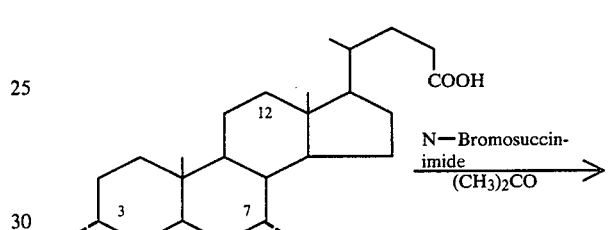

Chenodeoxycholic acid
(VII)

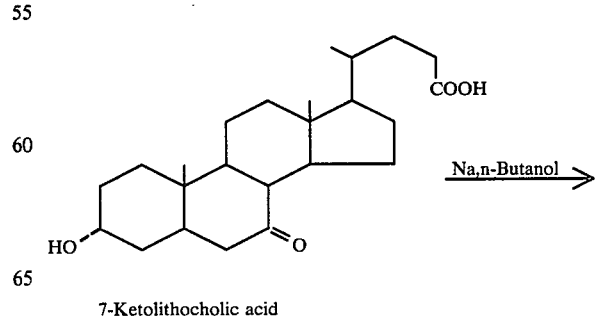

7-Ketolithocholic acid
(VIII)

The seventh or final step is to reduce 7-ketolithocholic acid (VIII) under a catalytic reduction process carried out in n-butanol, thus obtaining the final product, ursodeoxycholic acid (I), as shown below.

7-Ketolithocholic acid
(VIII)

-continued

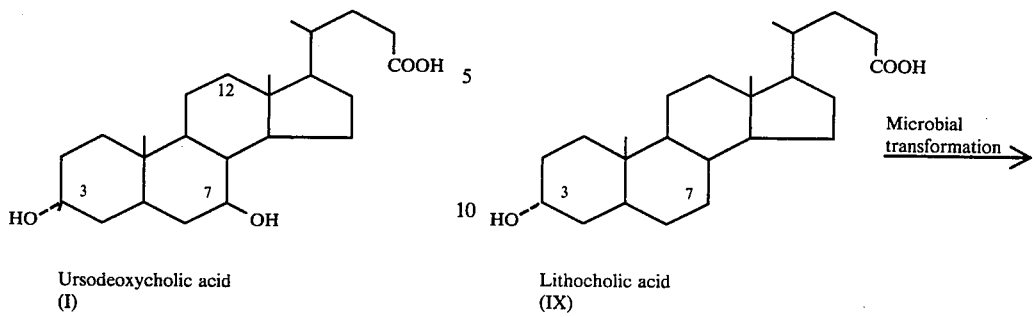

Ursodeoxycholic acid
(I)

Lithocholic acid
(IX)

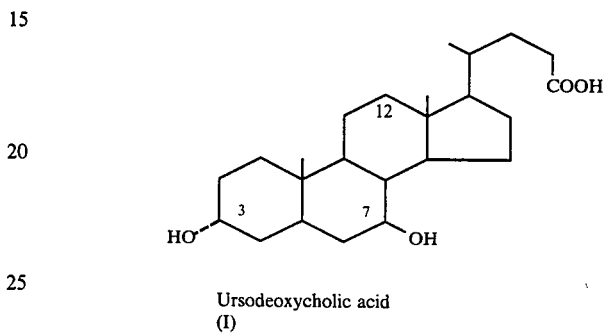

Ursodeoxycholic acid
(I)

Since the foregoing process for production of ursodeoxycholic acid available in the prior art comprises 7 independent steps each of which requires a purification process thereafter, the process has various drawbacks such as being complicated, insufficient productivity, etc.

Further, the process results in a low yield caused by various undesirable side reactions which are likely to accompany each of the foregoing independent steps.

PRIOR ART STATEMENT

Saltzman has disclosed in U.S. Pat. No. 3,954,562 a one-step method for production of 12-dihydro steroids, typically chenodeoxycholic acid, by means of a microbial transformation technique which comprises subjecting 12-hydroxy steroids, typically cholic acid, to the action of a 12-dehydroxylase producing microorganism, e.g. a microorganism belonging to Clostridium or Bifidobacterium. Sawada has also disclosed in a Japanese Patent Application which was laid open to public inspection as No. Toku-Kai-Sho 56-51997, a one-step method for production of 12-ketochenodeoxycholic acid which comprises subjecting dehydrocholic acid to the action of a microorganism belonging to Lactobacillus.

However, neither of the foregoing methods refers to production of ursodeoxycholic acid.

In our best knowledge, no method is available in the prior art for production of ursodeoxycholic acid by means of a microbial transformation technique.

OBJECTS AND SUMMARY OF THE INVENTION

An object of the present invention is to provide a one-step method for production of ursodeoxycholic acid from lithocholic acid, the starting material, by means of a microbial transformation technique, which is entirely free of the foregoing drawbacks such as being complicated, insufficient productivity, low yield, etc.

A method, in accordance with the present invention, for production of ursodeoxycholic acid (I) by means of a microbial transformation technique, comprises subjecting lithocholic acid (IX), the starting material, to the action of any of the microorganisms or molds belonging to *Fungi imperfecti* and further belonging to Fusarium, thereby specifically replacing a hydrogen atom located at the 7β position of lithocholic acid (IX) with a hydroxyl group, thus producing ursodeoxycholic acid (I).

More specifically, the method in accordance with the present invention comprises a step of cultivating any of the ursodeoxycholic acid producing microorganisms belonging to Fusarium, typically *Fusarium equiseti* strain M-41 (hereinafter referred to as Strain M41), a step of bringing lithocholic acid, the starting material, into contact with the foregoing microorganism or any part thereof, such as spores, conidia, mycelia et al. in any manner, namely in any type of reaction liquids, such as a nutrient medium, a reaction medium et al., and a step of recovering produced ursodeoxycholic acid, the final product. In other words, this method allows a wide variety in the manner in which lithocholic acid is brought into contact with the microorganism or the parts thereof. Namely, the microbial transformation which this invention is directed to, is allowed to occur in any type of reaction liquids, including a nutrient medium, a reaction medium, etc. In this specification, the nutrient medium is defined as a medium in which the microorganism is cultivated, and the reaction medium is defined as a medium which readily allows the foregoing microbial transformation to occur therein.

Embodiments of the present invention are as follows:

(1) A method for production of ursodeoxycholic acid defined above, wherein the step of bringing lithocholic acid into contact with the microorganism or any part thereof is allowed to occur in a medium in which the cultivation of the ursodeoxycholic acid producing microorganism is carried out.

(2) A method for production of ursodeoxycholic acid defined above, (a) which further comprises a step of harvesting the ursodeoxycholic acid producing microorganism and a step of preparing a reaction medium which contains the harvested microorganism or any part thereof, and (b) in which the step of bringing lithocholic acid into contact with the microorganism or any part thereof is allowed to occur in the foregoing reaction medium.

(3) A method for production of ursodeoxycholic acid defined above, (a) in which the step of cultivating the ursodeoxycholic acid producing microorganism is carried out until spores are formed, (b) which further comprises a step of collecting the spores and a step of preparing a reaction medium which contains the collected spores, and (c) in which the step of bringing the lithocholic acid into contact with the microorganism or any part thereof is allowed to occur in the foregoing reaction medium which contains the collected spores.

The foregoing embodiment (1) is directed to a method wherein the microbial action for production of ursodeoxycholic acid proceeds in a mixture of the ursodeoxycholic acid producing microorganism or its part, e.g. spores, conidia and mycelia, the nutrient medium and lithocholic acid. Therefore, no limitation is imposed for the time at which lithocholic acid is added to the medium containing the ursodeoxycholic acid producing microorganism or the part thereof.

The foregoing embodiment (2) is directed to a method wherein the microbial action for production of ursodeoxycholic acid proceeds in a mixture of the ursodeoxycholic acid producing microorganism or its part, e.g. spores, conidia and mucelia, the reaction medium and lithocholic acid, such a mixture being provided in the form of either a solution or suspension. The microorganism can be employed either immediately after cultivation or after recovery for some length of time in a fixed form which is readily realized by employment of a fixing agent such as calcium arginate, etc.

It is noted that although the foregoing embodiment (2) is originally a kind of batch process, a continuous process is also available, in which lithocholic acid is continuously supplied to contact a lump of the fixed microorganisms.

The foregoing embodiment (3) is directed to a method wherein only the spores of the ursodeoxycholic acid producing microorganism are employed for the microbial action for production of ursodeoxycholic acid. Some organic materials, typically some carbohydrate such as glucose, and casein hydrolysate, etc., are effective to enhance the reaction, when they are additionally supplied to the reaction medium. It is of course allowed for the spores to be employed in a fixed form as is in the case of the embodiment (2), and a continuous process is also available, as is in the case of the embodiment (2).

BRIEF DESCRIPTION OF THE DRAWING

The present invention, together with its various features and advantages, can be readily understood from the following more detailed description in conjunction with the FIGURE which is a photograph showing the appearance of Strain M-41, a microorganism belonging to *Fusarium equiseti*, which is an example of the ursodeoxycholic acid producing strain in accordance with the present invention.

DETAILED DESCRIPTION

Identification of Strain M-41

In the early phase of cultivation of Strain M-41 carried out at 30° C. on a potato dextrose agar medium, a single phialide grows on the side of a conidiophore, before macroconidia grow on the foregoing phialide. The size (specifically the dimension of cross-sectional area of the phialide) ranges $2.5 \times 10$ μm through $3 \times 12.5$ μm.

Sporodochia never grow on the conidiophore. In two weeks, the end of the conidiophore splits in the form of a broom, and 2 through 4 phialides grow at the split end of the conidiophore. The phialides having an obclavate shape are slightly larger than the phialides which previously grew at the side of a conidiophore, and the size of the phialides ranges $3 \times 12$ μm through $4 \times 17$ μm.

The macroconidia have a variety of shapes including a spindle and a crescent. The macroconidia are slim and both ends thereof become narrower to be discontinued with sharp ends. Most macroconidia have 5 septa and have the size range of $3.8 \times 50$ μm through $4.5 \times 63$ μm. A few macroconidia have 3 septa and have the size range of $3.8 \times 30$ μm through $4.8 \times 38$ μm.

It is quite seldom that microconidia grow.

Spherical or oval chlamydospores are formed on a mycelium. The spherical ones have the diameter range of 7-9 μm, and the oval ones have a longer diameter ranging from 11 to 12.5 μm and a shorter diameter ranging from 5 to 8.7 μm.

Four-day cultivation carried out on a potato dextrose agar medium allows Strain M-41 to grow to a colony whose diameter is 4.4 cm at 31° C., 5.8 cm at 27° C. and 5.5 cm at 25° C.

Two-month cultivation carried out on a corn agar medium, an oatmeal agar medium or a potato agar medium does not allow Strain M-41 to form ascocarps, ascus or ascospores.

FIG. 1 is a photograph wherein the magnification is 600 showing the appearance of Strain M-41 which was cultivated for 14 days on an oatmeal agar medium containing 30 grams of oatmeal, 20 grams of agar and 1 liter of water and having the pH of 6.5.

In accordance with Booth's classification (Booth C, the Genus Fusarium: Commonwealth Mycological Institute, Kew, Surrey (1971)), Strain M-41 described above was identified as *Fusarium equiseti* and named as *Fusarium equiseti* M-41. This is because the appearance of Strain M-41 is identical to the reference appearance of *Fusarium equiseti* (Corda) Sacc., Sylloge Fung., except that the length (5 μm) of some of the macroconidia having 5 septa is rather longer than the Booth's reference. Strain M-41 has been deposited at Fermentation Research Institute, Agency of Industrial Science & Technology, Japan with the Deposition No. FERM-P6351.

The physiological properties of Strain M-41 are as follows:

(1) Optimum growth conditions (pH and temperature)

The optimum pH range is 6 through 6.5, and the optimum temperature range is 27° through 28° C.

(2) Allowable growth conditions (pH and temperature)

The allowable pH range is 3.5 through 8, and the allowable temperature range is 10° through 37° C.

(3) Other specific feature

In the last phase of cultivation carried out on a Czapek agar medium or in a liquid medium, the color of spores of the strain becomes pale pink.

Screening of Strain M-41

609 independent mold strains were isolated from the soil picked up at 6 independent places in and adjacent to Osaka Prefecture, Japan. Each of these strains was inoculated in 20 ml of a basal medium containing lithocholic acid which is kept in a 100-ml triangular flask to be incubated on a shaker at 28° C. for 5 days. After completion of the incubation, the pH was adjusted to 3 with 5N hydrochloric acid, before bile acids were extracted with 50 ml of ethyl acetate. After being dehydrated with Glauber's salt, the extract was vacuumcondensed by means of a rotary evaporator. Qualitative analysis was applied to each of the condensed extracts by means of thin layer chromatography, for the purpose of screening a strain which is capable of producing ursodeoxycholic acid. In the foregoing thin layer chromatography, the bands for each of the condensed extracts were compared with that for the standard ursodeoxycholic acid. In this manner, we were successful in screening a strain which is capable of producing ursodeoxycholic acid from lithocholic acid. The screened strain was named Strain M-41. The mold strain from which we were successful in screening Strain M-41 was isolated from the soil picked up at a hill in Minoo, Osaka Prefecture, Japan on July 28, 1981.

The basal medium employed for isolation of the strain contained 1 liter of water, 30 gr. of glucose, 3 gr. of sodium nitrate, 5 gr. of yeast extract, 2 gr. of monopotassium phosphate, 3 gr. of dipotassium phosphate, 0.5 gr. of magnesium sulfate, 0.5 gr. of calcium chloride, 20 mg of iron(I) sulfate and 0.5 gr. of lithocholic acid which is the substrate to be transformed.

EXAMPLE 1

A medium is prepared by mixing 1 liter of water with 50 gr. of glucose, 3 gr. of $NaNO_3$, 3 gr. of $K_2HPO_4$, 2 gr. of $KH_2PO_4$, 0.5 gr. of $MgSO_4.7H_2O$, 0.5 gr. of KCl, 20 mg of $FeSO_4$ and 0.5 gr. of lithocholic acid. 6 liters of the medium is poured into a reaction tank having the capacity of 10 liters. On the other hand, Strain M-41 is incubated on a shaker at 28° C. for 24 hours employing the same medium as is described above to prepare a preculture. 0.3 liter of this preculture is inoculated in the foregoing medium to be cultivated under an aerobic condition at 28° C. for 3 days. During the cultivation, the mixture is stirred at the rate of 300 rpm, the pH is adjusted to 7, and air is supplied at the rate of 0.5 vvm. After completion of the cultivation, hydrochloric acid is added to the culture to adjust the pH to 3. Thereafter, an extraction process is applied to the culture three times with 2 volumes of ethyl acetate for the purpose of collecting (a) the produced ursodeoxycholic acid, and (b) the remaining lithocholic acid, out of the residual medium containing the ursodeoxycholic acid producing microorganism. The resultant ethyl acetate layer which contains the foregoing materials including (a) ursodeoxycholic acid and (b) lithocholic acid, is washed with water. Thereafter, anhydrous Glauber's salt is added for the purpose of dehydration. Thereafter, ethyl acetate is evaporated under vacuum to obtain a residue containing (a) the produced ursodeoxycholic acid and (b) the remaining lithocholic acid. This residue is applied to a column containing 80 gr. of silica gel (Wako gel C-200), before he column is further applied with a mixture of solvents containing chloroform, acetone and acetic acid at the volumetric ratio of 100:100:1 for the purpose of eluting ursodeoxycholic acid. Thereafter, the fractions which contain ursodeoxycholic acid in the foregoing solvent mixture are selectively gathered. In this manner, the produced ursodeoxycholic acid is readily separated from the starting material, lithocholic acid. Further, a purification process is carried out in the following manner. The solvents are removed from the fraction by means of evaporation, leaving the produced ursodeoxycholic acid. The remaining material, predominantly containing the produced ursodeoxycholic acid, is dissolved in a small quantity of ethanol. The ethanol solution is applied to a preparative thin layer of silica gel (Merck Kieselgel G-60, $F_{254}$, 2-mm thick) for the purpose of developing the foregoing ursodeoxycholic acid employing the foregoing mixture of solvents. After the developing process, the silica gel layer is dried, a band of the thin layer of silica gel containing ursodeoxycholic acid is precisely sliced, before the ursodeoxycholic acid is extracted therefrom with ethanol. The extract containing ursodeoxycholic acid is condensed, before the ursodeoxycholic acid is allowed to crystallize out of a mixture of ethanol and water. A further purification process could be employed wherein ursodeoxycholic acid is recrystallized out of an ethyl acetate solution.

The yield of ursodeoxycholic acid is 0.25 gr. out of 1 liter of culture or 0.5 gr. of lithocholic acid, the starting material, representing 50 weight % yield for ursodeoxycholic acid based on the lithocholic acid.

EXAMPLE 2

An aerobic cultivation process similar to that which is described for Example 1 is employed to incubate Strain M-41 in a reaction tank containing 6 liters of a medium (pH 7.0) prepared by mixing 1 liter of water with 50 gr. of oatmeal and 0.1 gr. of lithocholic acid. After the cultivation is continued for 24 hours, 0.5 gr./liter of lithocholic acid is additionally supplied, before a further cultivation is carried out for 48 hours.

After completion of the cultivation, the purification process identical to that which is described for Example 1 is employed to extract and isolate the produced ursodeoxycholic acid. The yield of ursodeoxycholic acid is 0.28 gr. out of 1 liter of culture or 0.6 gr. of lithocholic acid, representing 47 weight % yield for ursodeoxycholic acid based on the lithocholic acid.

EXAMPLE 3

A medium is prepared by mixing 1 liter of water with 20 gr. of starch, 50 gr. of corn steep liquor, 5 gr. of beef extract, 5 gr. of polypeptone, 5 gr. of sodium chloride and 0.5 gr. of lithocholic acid. Strain M-41 is incubated in 6 liters of the medium contained in a reaction tank. Cultivation is carried out at 28° C. for 36 hours, while the pH is maintained at 7.

After completion of the cultivation, the cultivated microorganism is collected by means of centrifugation. The collected microorganism is washed with a phosphate buffer (pH 7.0). On the other hand, a reaction medium (pH 7.0) is prepared by mixing 1 liter of water with 2 gr. of monopotassium phosphate, 3 gr. of dipotassium phosphate, 10 gr. of glucose and 0.2 gr. of lithocholic acid. The foregoing collected microorganism is added to this reaction medium to make a suspension containing 30 gr. of the microorganism in 1 liter of the medium. A conversion reaction is carried out under aeration in this suspension at 28° C. for 48 hours.

After completion of the conversion reaction, the purification process identical to that which is described for Example 1 is employed to extract and isolate the produced ursodeoxycholic acid. The yield of ursodeoxycholic acid is 0.1 gr. out of 1 liter of reaction medium or 0.2 gr. of lithocholic acid, representing 50 weight % yield for ursodeoxycholic acid based on the lithocholic acid.

EXAMPLE 4

An agar medium (pH 7) is prepared by mixing 1 liter of water with 30 gr. of oatmeal, 0.2 gr. of lithocholic acid and 20 gr. of agar. Strain M-41 is aerobically cultivated on the agar medium at 28° C. for 2 weeks.

After completion of the cultivation, the cultivated microorganisms are suspended in a phosphate buffer (pH 7.0). After mycelia are filtered with a gauze filter out of the suspension, the spores remaining in the suspension are collected by means of centrifugation. The collected spores are washed with water.

The spores are poured in a phosphate buffer (pH 7.0) to produce a reaction medium containing $10^{10}$ spores in 1 milliliter thereof.

2 gr. of glucose and 0.2 gr. of lithocholic acid are added to 1 liter of the reaction medium for the purpose of allowing a conversion reaction to occur therein at 30° C. for 48 hours under aseptic aeration.

After completion of the conversion reaction, the purification process identical to that which is described for Example 1 is employed to extract and isolate the produced ursodeoxycholic acid. The yield of ursodeoxycholic acid is 0.1 gr. out of 1 liter of the reaction medium or 0.2 gr. of lithocholic acid, representing 50 weight % yield for ursodeoxycholic acid based on the lithocholic acid.

Identification of Produced Ursodeoxycholic Acid with Reference Ursodeoxycholic Acid Firstly, a thin layer chromatography (Merck Kieselgel G-60, $F_{254}$, 0.25-mm thick) was employed to identify each of the products of Examples 1 through 4 with the standard (ursodeoxycholic acid supplied by Gasukuro Kogyo Co., Ltd.). The Rf values determined for each of the products of Examples 1 through 4 precisely met with the Rf values determined for the standard ursodeoxycholic acid for each of the developing solvent systems tabulated below.

| Developing Solvent System | Rf Value |
| --- | --- |
| 1. Diethyl ether:acetic acid (249:1) | 0.16 |
| 2. Chloroform:acetone:acetic acid (100:100:1) | 0.49 |
| 3. 2,2,4-trimethyl pentane:ethyl acetate: acetic acid:butanol (20:10:3:3) | 0.45 |
| 4. 2,2,4-trimethyl pentane:isopropanol: acetic acid (60:20:0.5) | 0.36 |
| 5. 2,2,4-trimethyl pentane:ethyl acetate: acetic acid (5:1:1) | 0.35 |
| 6. Chloroform:methanol:acetic acid (80:12:3) | 0.75 |
| 7. Chloroform:methanol:water (70:25:3) | 0.72 |
| 8. 2,2,4-trimethyl pentane:diisopropyl ether:acetic acid:butanol:water (10:5:5:3:1) | 0.36 |
| 9. Chloroform:ethyl acetate:acetic acid (9:9:2) | 0.54 |
| 10. 2,2,4-trimethyl pentane:acetic acid: diisopropyl ether:isopropanol (10:6:5:1) | 0.51 |
| 11. Chloroform:methanol:7N $NH_4OH$:water (21:15:1:2) | 0.78 |
| 12. 2,2,4-trimethyl pentane:diisopropyl ether:acetic acid:isopropanol (2:1:1:1) | 0.77 |
| 13. Isopropanol:ethyl acetate:water: $NH_4OH$ (20:25:6:4) | 0.38 |
| 14. 2,2,4-trimethyl pentane:diisopropyl ether:acetic acid:butanol:isopropanol: water (10:5:5:3:6:1) | 0.80 |
| 15. Propanol:acetic acid:water (95:4:1) | 0.87 |
| 16. Butanol:acetic acid:water (100:7:5) | 0.89 |
| 17. Ethyl acetate:methanol:acetic acid (7:2:1) | 0.87 |

Additionally, various analyses tabulated below were applied to each of the products of Examples 1 through 4 to identify each of them with the foregoing standard ursodeoxycholic acid.

1. Elemental analysis
2. Melting point test and mixed melting point test
3. Infrared spectrum analysis
4. Mass spectrum analysis
5. Nuclear magnetic resonance spectrum analysis The results of all the foregoing tests determined that the properties of each of the products of Examples 1 through 4 precisely meet those of the standard ursodeoxycholic acid.

Conclusion

The foregoing description has clarified that a one-step method for production of ursodeoxycholic acid from lithocholic acid by means of microbial transformation is successfully provided, and that the method in accordance with the present invention is entirely free of the drawbacks inherent to any method available in the prior art, namely, being complicated, insufficient productivity and low yield. In other words, the method in accordance with the present invention has various features including simplicity of the process, sufficient productivity and sufficient yield.

Although the present invention has been described with reference to a specific strain, Strain M-41 having its Deposition No. FERM-P6351, this is not meant to be construed in a limiting sense. Various modifications of the described embodiment, as well as other embodiments based on any of the microorganisms or molds belonging to Fusarium, will become apparent to persons skilled in the art upon reference to the description of the present invention. It is therefore contemplated that the apended claims will cover any such modifications or embodiments as fall within the true scope of this invention.

What is claimed is:

1. A method of producing ursodeoxycholic acid by means of microbial transformation comprising:
   cultivating an ursodeoxycholic acid producing microorganism of *Fusarium equiseti* FERM-P6351,
   bringing lithocholic acid into contact with said microorganism to convert said lithocholic acid to ursodeoxycholic acid, and
   recovering said ursodeoxycholic acid.

2. A method as defined in claim 1, wherein said lithocholic acid is brought into contact with said microorganism in a medium in which said microorganism is being cultivated.

3. A method as defined in claim 1, which further comprises harvesting the cultivated microorganism and preparing a reaction medium which contains the harvested microorganism, said lithocholic acid being brought into contact with said microorganism in said reaction medium.

4. A method as defined in claim 1, wherein said microorganism is cultivated until spores thereof are formed, and the method further comprises collecting said spores and preparing a reaction medium which contains the collected spores, said lithocholic acid being brought into contact with said spores in said reaction medium.

5. A method for producing ursodeoxycholic acid by means of microbial transformation comprising:
   preparing a reaction liquid which contains a part of an ursodeoxycholic acid producing microorganism of *Fusarium equiseti* FERM-P6351,
   bringing lithocholic acid into contact with said reaction liquid to convert said lithocholic acid to ursodeoxycholic acid, and
   recovering said ursodeoxycholic acid.

* * * * *

UNITED STATES PATENT AND TRADEMARK OFFICE
CERTIFICATE OF CORRECTION

PATENT NO. : 4,579,819
DATED : April 1, 1986
INVENTOR(S) : Haruji Sawada and Hisaharu Taguchi It is certified that error appears in the above-identified patent and that said Letters Patent are hereby corrected as shown below:

Column 3, line 60, change "Huang-Minion" to --Huang-Minlon--.
Column 7, line 22, change "mucelia" to --mycelia--.
Column 8, line 44, change "p6351" to --BP-259--.
Column 9, line 55, change "he" to --the--.
Column 12, lines 26, 39 and 63 change "FERM-P6351" (each occurrence) to --FERM BP-259--.

Signed and Sealed this

Twenty-fifth Day of November, 1986

Attest:

DONALD J. QUIGG

Attesting Officer          Commissioner of Patents and Trademarks